United States Patent [19]
Behler et al.

[11] Patent Number: 5,349,106
[45] Date of Patent: Sep. 20, 1994

[54] PROCESS FOR REDUCING THE RESIDUAL CONTENT OF FREE ALKYLATING AGENT IN AQUEOUS SOLUTIONS OF CATIONIC SURFACTANTS

[75] Inventors: Ansgar Behler, Bottrop; Uwe Ploog; Hermann Hensen, both of Haan; Guenter Uphues, Monheim, all of Fed. Rep. of Germany

[73] Assignee: Henkel Kommanditgesellschaft auf Aktien, Duesseldorf, Fed. Rep. of Germany

[21] Appl. No.: 971,963

[22] PCT Filed: Aug. 10, 1991

[86] PCT No.: PCT/EP91/01526

§ 371 Date: Feb. 18, 1993

§ 102(e) Date: Feb. 18, 1993

[87] PCT Pub. No.: WO92/03406

PCT Pub. Date: Mar. 5, 1992

[30] Foreign Application Priority Data

Aug. 18, 1990 [DE] Fed. Rep. of Germany ....... 4026184

[51] Int. Cl.$^5$ .............................................. C07C 209/84
[52] U.S. Cl. ..................... 564/282; 564/285; 564/288; 564/291; 564/292; 564/296
[58] Field of Search ............... 564/282, 285, 288, 291, 564/292, 296

[56] References Cited

U.S. PATENT DOCUMENTS

| | | | |
|---|---|---|---|
| 2,692,286 | 10/1954 | Stayner et al. ...................... | 564/285 |
| 3,755,334 | 8/1973 | Sommer ............................... | 564/292 |
| 4,766,149 | 8/1988 | Osswald et al. .................... | 514/553 |
| 4,845,289 | 7/1989 | Ries et al. ........................... | 564/296 |
| 4,992,263 | 2/1991 | Tesmann et al. ................... | 424/63 |

FOREIGN PATENT DOCUMENTS 0178846 9/1985 Japan .

OTHER PUBLICATIONS

Patent Abstracts of Japan (Unexamined Applications), C Field, vol. 10, No. 28, Published on Feb. 4, 1986, The Patent Office, Japanese Government, p. 7, C 326, See JP-A-60-178846.

Soviet Inventions Illustrated, Section Ch, Week C 30, Published on Sep. 3, 1980, Derwent Publications Ltd., London, D 25, See SU-702-003 (Belorussian Lenin Univ.).

J. Falbe (ed.), "Surfactants in Consumer Products", Springer Verlag, Berlin, 1987, pp. 107-114.

*Primary Examiner*—Peter O'Sullivan
*Attorney, Agent, or Firm*—Ernest G. Szoke; Wayne C. Jaeschke; Henry E. Millson, Jr.

[57] ABSTRACT

A process for reducing the residual content of free alkylating agent in aqueous solutions of cationic surfactants comprising aftertreating the solutions with at least one of the following amine compounds:

a) ammonia;
b) tertiary amine corresponding to the general formula (I)

$$R^1-\underset{\underset{R^3}{|}}{\overset{\overset{R^2}{|}}{N}}\hspace{1em}(I)$$

in which $R^1$, $R^2$ and $R^3$ independently of one another represents linear or branched, optionally hydroxy-substituted alkyl radicals containing 1 to 18 carbon atoms or an alkenyl radical containing 8 to 18 carbon atoms;

c) amino acids containing 2 to 8 carbon atoms; and
d) oligopeptides having an average molecular weight of about 500 to about 5000, at an elevated temperature.

15 Claims, No Drawings

PROCESS FOR REDUCING THE RESIDUAL CONTENT OF FREE ALKYLATING AGENT IN AQUEOUS SOLUTIONS OF CATIONIC SURFACTANTS

This invention relates to a process for reducing the residual content of free alkylating agent in aqueous solutions of cationic surfactants by aftertreatment of the solutions with an amine compound.

Cationic surfactants of the quaternary ammonium compound type are important products for the production of fabric softeners, hair conditioners, antistatic agents and disinfectants. They are generally synthesized from tertiary amines by reaction with an alkylating agent, for example methyl chloride, benzyl chloride or dimethyl sulfate (J. Falbe (ed.), "Surfactants in Consumer Products", Springer Verlag, Berlin, 1987, pages 107–114).

Since the alkylation is not quantitative, quaternary ammonium compounds produced by the methods mentioned above have a residual content of 0.1 to 3% by weight of the alkylating agent in the absence of an aftertreatment. Since it is necessary for obtaining toxicologically safe products to reduce the content of methyl chloride, benzyl chloride or dimethyl sulfate in the products to as low a level as possible, there has been no shortage of attempts in the past to achieve this goal by suitable working up. In this way, the content of free alkylating agent is normally reduced to a small amount by heat treatment for several hours. However, this procedure is highly time- and energy-consuming.

Accordingly, the problem addressed by the present invention was to provide a new process for the aftertreatment of cationic surfactants which would enable the content of free alkylating agent to be distinctly reduced and which would be free from the disadvantages mentioned above.

The present invention relates to a process for reducing the residual content of free alkylating agent in aqueous solutions of cationic surfactants, characterized in that the solutions are aftertreated with an amine compound selected from the group consisting of
a) ammonia,
b) tertiary amines corresponding to general formula (I)

in which $R^1$, $R^2$ and $R^3$ independently of one another represent linear or branched, optionally hydroxy-substituted alkyl radicals containing 1 to 18 carbon atoms or alkenyl radicals containing 8 to 18 carbon atoms,
c) amino acids containing 2 to 8 carbon atoms and
d) oligopeptides having an average molecular weight of 500 to 5000,
at elevated temperature and optionally elevated pressure.

It has surprisingly been found that this method of working up leads to lower residual contents of free alkylating agent in the cationic surfactant solutions in distinctly shorter times by comparison with the thermal aftertreatment. The invention is based on the observation that the amine compounds react off quickly and completely with the alkylating agent at elevated temperature.

Cationic surfactants in the context of the invention are known chemical substances and correspond to general formula (II)

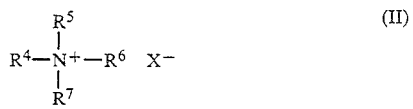

in which $R^4$, $R^5$ and $R^6$ independently of one another represent linear or branched, optionally hydroxy-substituted alkyl radicals containing 1 to 18 carbon atoms or alkenyl radicals containing 8 to 18 carbon atoms, $R^7$ is a linear or branched alkyl radical containing 1 to 4 carbon atoms or a phenyl radical and X is a halide ion, preferably chloride or bromide, or the anion of methyl sulfuric acid.

Alkylating agents in the context of the invention are benzyl chloride, dimethyl sulfate and, in particular, methyl chloride.

Suitable tertiary amines are linear or branched, but above all hydroxy-substituted trialkyl amines, such as for example triethanolamine, dimethyl ethanolamine or 3-dimethylaminopropanol.

Suitable $C_{2-8}$ amino acids for the aftertreatment of the cationic surfactant solutions are alanine, arginine, asparagine, cystein, cystine, dibromotyrosine, diiodotyrosine, glutamine, glutamic acid, histidine, hydroxylysine, hydroxyproline, isoleucine, leucine, lysine, methionine, phenyl alanine, proline, serine, threonine, thyroxine, tryptophan, tyrosine and valine. The aftertreatment is preferably carried out with glycine.

The aftertreatment may also be carried out with oligopeptides which have a sufficiently low degree of oligomerization to be completely soluble in water under in-use conditions and in the in-use concentration, for example oligopeptides having an average molecular weight of 500 to 5000. Water-soluble products of the type obtained, for example, in the partial hydrolysis of proteins, for example gelatine or collagen (Angew. Chem. 90, 187 (1978)), are particularly suitable for this purpose.

The aftertreatment of the aqueous solutions of cationic surfactants may be carried out by addition of 0.1 to 10% by weight and preferably 0.5 to 3% by weight, based on the surfactant solution, of the amine compound. The aftertreatment is preferably carried out with 0.5 to 3.0% by weight, based on the surfactant solution, of a 25 to 80% by weight aqueous and/or alcoholic solution of ammonia or, more particularly, glycine.

The aftertreatment of the cationic surfactant solutions is carried out by heating the solutions with the aftertreatment agent for 1 to 4 h and preferably for 1 to 2 h at a pH value of 7.5 to 9.5, which is automatically established, and at a temperature of 60° to 98° C. and preferably at a temperature of 70° to 90° C. In general, the reduction in the residual content of alkylating agent takes place more quickly, the higher the aftertreatment temperature. The aftertreatment normally takes place at normal pressure. However, it may also be carried out at elevated pressure, for example of 1 to 2 bar, and at a temperature of up to 120° C. in a pressurized autoclave in order to accelerate the reaction.

The residual content of free alkylating agent, more particularly methyl chloride, is reduced by the aftertreatment to values below 5 ppm, based on the solids content of the surfactant solution, in 1 to 4 hours.

The following Examples are intended to illustrate the invention without limiting it in any way.

EXAMPLES

Starting material

A 25% by weight aqueous solution of cetyl trimethyl ammonium chloride (A) obtainable by alkylation of cetyl dimethyl amine with methyl chloride was used as the starting material. The free methyl chloride content was 900 ppm.

EXAMPLES 1 TO 3

200 g (0.6 mol) A were introduced into a 500 ml three-necked flask equipped with a stirrer, reflux condenser and internal thermometer and 0.5 g, corresponding to 1% by weight, based on the solids content of the cationic surfactant solution, of an amine compound was added. The reaction mixture was heated over a period t of 1 to 2 h at pH =8 to 8.5 and at a temperature T of 90° C. and was then cooled to room temperature. The residual content of methyl chloride was determined by gas chromatography. The results are set out in Table 1.

COMPARISON EXAMPLES C1 TO C3

In an apparatus corresponding to Example 1, 200 g A were thermally aftertreated without an amine compound at pH 8 to 8.5, T =90° C. and t =1 to 3 h and the residual content of methyl chloride was determined. The results are set out in Table 1.

TABLE 1

| | Aftertreatment of A | | |
| --- | --- | --- | --- |
| Ex. | Amino compound | Quantity used % by weight | t h | Methyl chloride content ppm |
| 1 | Glycine | 1 | 1 | <5 |
| 2 | Ammonia | 1 | 1 | 10 |
| 3 | Ammonia | 1 | 2 | <5 |
| C1 | — | — | 1 | 140 |
| C2 | — | — | 2 | 43 |
| C3 | — | — | 3 | 23 |

We claim:

1. A process for reducing the residual content of free alkylating agent in an aqueous solution of a cationic surfactant comprising aftertreating said aqueous solution at a temperature above about 60° C. with at least one amine compound selected from the group consisting of
   a) an amino acid containing 2 to 8 carbon atoms; and
   b) an oligopeptide having an average molecular weight of about 500 to about 5000.
2. The process of claim 1 wherein the at least one amine compound is glycine.
3. The process of claim 1 wherein from about 0.1% to about 10% by weight, based on the surfactant solution, of the at least one amine compound is employed for the aftertreatment.
4. The process of claim 1 wherein the aftertreatment is carried out for a period of from about 1 to about 4 hours at a pH of from about 7.5 to about 9.5 and at a temperature in the range of from about 60° C. to about 98° C.
5. The process of claim 1 wherein the temperature is in the range of from about 70° C. to about 90° C.
6. The process of claim 1 wherein the temperature is up to about 120° C. at a pressure of from about 1 to about 2 bar.
7. The process of claim 1 wherein the at lest one amine compound employed is in the form of an about 25% to about 80% by weight aqueous and/or alcoholic solution.
8. The process of claim 7 wherein the at least one amine compound is glycine.
9. The process of claim 1 wherein the cationic surfactant has the following formula

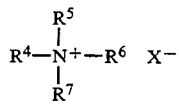

wherein $R^4$, $R^5$ and $R^6$ independently of one another represent a linear or branched, optionally hydroxy-substituted alkyl radical containing 1 to 18 carbon atoms or an alkenyl radical containing 8 to 18 carbon atoms, $R^7$ is a linear or branched alkyl radical containing 1 to 4 carbon atoms or a phenyl radical, and X is a halide ion, or the anion of methyl sulfuric acid.

10. The process of claim 1 wherein the at least one amine compound is at least one oligopeptide from the partial hydrolysis of proteins.
11. The process of claim 10 wherein the proteins are gelatin and/or collagen.
12. The process of claim 1 wherein the temperature is in the range of from about 60° C. to about 98° C., and from about 0.1% to about 10% by weight, based on the surfactant solution, of the at least one amine compound is present in the aqueous solution.
13. The process of claim 12 wherein the temperature is in the range of from about 70° C. to about 90° C.
14. The process of claim 12 wherein the at least one amine compound is glycine.
15. The process of claim 12 wherein the cationic surfactant has the following formula

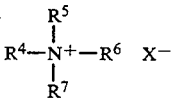

wherein $R^4$, $R^5$ and $R^6$ independently of one another represent a linear or branched, optionally hydroxy-substituted alkyl radical containing 1 to 18 carbon atoms or an alkenyl radical containing 8 to 18 carbon atoms, $R^7$ is a linear or branched alkyl radical containing 1 to 4 carbon atoms or a phenyl radical, and X is a halide ion, or the anion of methyl sulfuric acid.

* * * * *